United States Patent [19]

Schmidt

[11] 4,334,097
[45] Jun. 8, 1982

[54] PROCESS FOR THE PREPARATION OF N-α-ALKOXYALKYL-CARBOXAMIDES, AND SOME REPRESENTATIVES OF THIS CLASS OF COMPOUNDS AND SECONDARY PRODUCTS OBTAINED THEREFROM

[75] Inventor: Erwin Schmidt, Kelkheim, Fed. Rep. of Germany

[73] Assignee: Hoechst Aktiengesellschaft, Frankfurt am Main, Fed. Rep. of Germany

[21] Appl. No.: 259,367

[22] Filed: May 1, 1981

Related U.S. Application Data

[63] Continuation-in-part of Ser. No. 202,606, Oct. 31, 1980, abandoned.

[30] Foreign Application Priority Data

Nov. 3, 1979 [DE] Fed. Rep. of Germany ....... 2944456

[51] Int. Cl.$^3$ ............................................. C07C 102/00
[52] U.S. Cl. ............................. 564/201; 260/239.3 A; 546/220; 564/203; 564/215; 260/239 A; 548/551
[58] Field of Search ........................ 564/215, 201, 203; 260/239 AL, 239.3 A, 326.5 FN; 546/220

[56] References Cited

U.S. PATENT DOCUMENTS

| | | | |
|---|---|---|---|
| 3,914,304 | 10/1975 | Schnabel et al. | 564/215 |
| 4,118,500 | 10/1978 | Mitzlaff et al. | 546/220 |
| 4,138,400 | 2/1979 | Mitzlaff | 546/220 |
| 4,138,408 | 2/1979 | Mitzlaff et al. | 546/220 |
| 4,138,418 | 2/1979 | Warning et al. | 564/201 |
| 4,221,789 | 9/1980 | Rodriguez et al. | 260/239.3 A |

OTHER PUBLICATIONS

Böhme et al., Berichte, 99 (1966), pp. 2127–2135.

Finkelstein et al., Acta Chemica Scandanavia B32 (1978) pp. 182–186.

Primary Examiner—Arthur P. Demers
Attorney, Agent, or Firm—Curtis, Morris & Safford

[57] ABSTRACT

N-α-Alkoxyalkyl-carboxamides are prepared by reacting primary or secondary amides of aliphatic, araliphatic or aromatic carboxylic acids, or cyclic carboxamides (lactams) which are not capable of forming an aromatic system, with open-chain α-halogenoalkyl ethers with at least 3 C atoms per molecule, in the presence of tertiary amines. N,N-Bis-α-alkoxyalkylcarboxamides can also be obtained from the primary carboxiamides. The reaction products, of which the compounds V and VI:

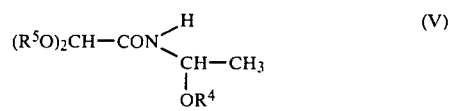

(V)

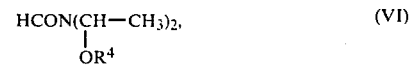

(VI)

wherein $R^4$=C-C$_4$-alkyl and $R^5$=CH$_3$ or C$_2$H$_5$, are new, are intermediates mainly for the preparation of N-alkenyl- or N-vinyl-carboxamides, of which, in turn, the compounds VII are new:

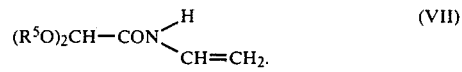

(VII)

The N-alkenyl- or N-vinyl-carboxamides can themselves be processed to give valuable homopolymers and copolymers.

11 Claims, No Drawings

PROCESS FOR THE PREPARATION OF N-α-ALKOXYALKYL-CARBOXAMIDES, AND SOME REPRESENTATIVES OF THIS CLASS OF COMPOUNDS AND SECONDARY PRODUCTS OBTAINED THEREFROM

This application is a continuation-in-part-application of Ser. No. 202,606 filed Oct. 31, 1980, now abandoned.

N-α-Alkoxyalkyl-carboxamides are valuable intermediates in various specialized fields, in particular in the field of polymers. To prepare polymers, alcohol is first split off from the N-α-alkoxyalkyl-carboxamides in accordance with known methods to give the corresponding N-alkenyl- or N-vinyl-carboxamides, and the latter can then in turn by polymerized to give homopolymers and copolymers with interesting and varied properties in application technology (dyeing auxiliaries especially in the textile industry, water soluble protection colloids, thickening agents, plastics with specific properties etc.); Ullmanns Enzyklopädie der technischen Chemie (Ullmann's Encyclopedia of Chemical Technology), 3rd edition, volume 14, pages 261–264).

A number of methods are known for the preparation of N-alkoxyalkyl-carboxamides. Secondary N-α-alkoxyalkyl-carboxamides, that is to say those carboxamides which still carry a free hydrogen atom on the nitrogen, are mainly prepared by electrochemical processes. A process for this type is described, for example, in German Offenlegungsschrift No. 2,113,338. According to this document, N-alkyl-carboxamides, inter alia, are alkoxylated with alcohols, using certain conducting salts, to give the corresponding N-α-alkoxyalkyl-carboxamides. According to this process, it should also be possible, in fact, to alkoxylate N-dialkyl-carboxamides to give the corresponding N-α-alkoxyalkyl-N-alkyl-carboxamides, that is to say tertiary N-α-alkoxyalkyl-carboxamides (without free hydrogen on the amido nitrogen), although the process is primarily suitable only for the preparation of secondary N-α-alkoxyalkyl-carboxamides because, in the case of 2 alkyl groups on the amido nitrogen, the alkoxylation only takes place on one alkyl group with a very poor selectivity, and the mixture formed is then very difficult to separate.

The electrochemical preparation of secondary N-α-alkoxyethyl-carboxamides from N-α-carboxyethylcarboxamides is described in German Offenlegungsschrift No. 2,336,976; however, the process first requires the preparation of the N-α-carboxyethyl-carboxamides which are necessary as starting materials, and this represents a certain effort.

The electrochemical process for the anodic alkoxylation of secondary N-ethyl-carboxamides according to Belgian Patent Specification No. 837,906 is more especially suitable for the preparation of secondary N-alkoxyethylcarboxamides; the process operates with a certain minimum current strength and very particular conducting salts.

It has furthermore been proposed (patent application Ser. No. P 2,919,756.6—HOE 79/F 118) to prepare secondary N-alkoxyethyl-carboxamides by the anodic alkoxylation of N-ethyl-carboxamides with an alcohol, in an electrolysis cell with vitreous carbon as the anode material and at least one alkali metal alkyl-sulfate and/or tetraalkylammonium alkyl-sulfate as the conducting salt.

In fact, the electrochemical processes described operate relatively cleanly and with good yields, but the technical effort associated with carrying them out is not insignificant. Moreover, the recovery of the necessary and often very considerable amounts of conducting salt, which is demanded on the grounds of environmental protection, frequently proves not to be very easy.

For the reasons mentioned in the discussion in German Offenlegungsschrift No. 2,113,338, tertiary N-α-alkoxyalkyl-carboxamides are hardly prepared by a purely electrochemical method, but mainly only chemically or partly electrochemically and partly chemically. A purely chemical method consists in reacting secondary N-alkyl-carboxamides with acetals or hemiacetals [Chemische Berichte, 99, 2,127 (1966); German Patent Specification No. 1,273,533]. The yields in this case are not always satisfactory, however, in particular as regards the straight-chain products. Thus, for example, a yield of only 26% is indicated in Example 11 of German Patent Specification No. 1,273,533 (reaction of N-methylacetamide with acetaldehyde diethylacetal to give N-α-ethoxyethyl-N-methylacetamide).

In accordance with a mixed electrochemical/chemical process proposed only recently (patent application No. P 2,919,755.5—HOE 79/F 119), N-ethylcarboxamides are first anodically alkoxylated with alcohols to give the corresponding N-α-alkoxyethyl-carboxamides, and the latter are then subjected to alkylation, for example by means of an alkyl halide in an alkaline medium, in accordance with the methods which are known in principle for alkylations of this type (Synthesis 1971, 966; Synthesis 1976, 113 et seq.; Z. Chem., 17 (1977), 260).

Although this process is very advantageous and favorable, it nevertheless appears to be in need of still further improvement, in particular because of the effort required to carry out the electrochemical process step.

In recent years, it has also become known to alkylate, on the nitrogen, a compound resembling a lactam (that is to say resembling a cyclic carboxamide), namely pyridin-2-one, with a cyclic α-halogenoalkyl ether, namely α-chloro-tetrahydrofuran (Tetrahedron Letters, 1976, 1,725 to 1,728—see, in particular, Example 17 in the table on page 1,727). The reaction can be represented by the following equation:

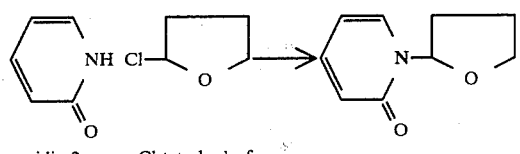

pyridin-2-one α-Cl-tetrahydrofuran

However, because of the possibility of the formation of an aromatic system, pyridin-2-one is not a "normal" lactam. According to L. F. Fieser and M. Fieser, "Lehrbuch der organischen Chemie" (Textbook of Organic Chemistry), Verlag Chemie, 1965, page 1,446, the isomeric and mesomeric forms of pyridin-2-one are as follows:

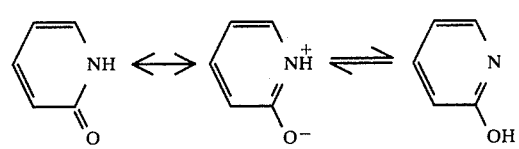

Because of the particular, already "pseudoaromatic" character of pyridin-2-one, it is also impossible to apply the reaction with an α-halogenotetrahydrofuran to "normal" carboxamides, as has been confirmed by our own experiments. In these experiments, for example, the "alkylation" of N-methylacetamide with an α-halogeno-tetrahydrofuran was not successful.

Similar reactions to that of pyridin-2-one with α-chloro-tetrahydrofuran are also known from nucleotide chemistry, in which "lactam-like" compounds which, in the same way as pyridin-2-one, are capable of forming an aromatic system, such as, for example, cytosine, guanine, thymine and the like, are likewise reacted with α-halogenosugars, for example

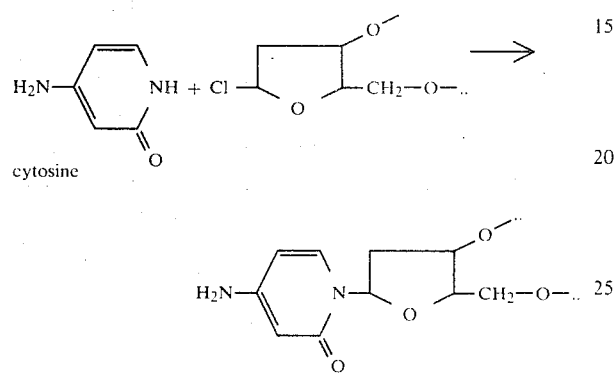

cytosine

These reactions cannot be used for the preparation of, for example, N-α-alkoxyalkyl derivatives of "normal" carboxamides (including cyclic carboxamides, that is to say lactams).

In an attempt further to improve the known processes for the preparation of N-α-alkoxyalkyl-carboxamides, it has now been found that this object, starting from primary or secondary carboxamides, can be achieved by reacting primary or secondary amides of aliphatic, araliphatic or aromatic carboxylic acids, or cyclic carboxamides (lactams) which are not capable of forming an aromatic system, with open-chain α-halogenoethers with at least 3 C atoms per molecule, in the presence of tertiary amines.

The success of this reaction, with the good to very good yields achieved in every case, was exceptionally surprising because, in view of the fact that the reaction of pyridin-2-one with α-chloro-tetrahydrofuran, known from Tetrahedron Letters, 1976, 1,725 et seq., no longer proceeds when the pyridin-2-one is replaced by a "normal" carboxamide, such as, for example, N-methylacetamide, it could not be expected that attempts to effect N-"alkylation" of "normal" carboxamides with α-halogenoalkyl ethers could in any way result in success. The fact that this success is indeed achieved when openchain α-halogenoalkyl ethers are used in place of the cyclic α-chloro-tetrahydrofuran was not in any way, even only remotely predictable.

The known N-alkylations of carboxamides with normal halogenoalkyl compounds, such as, for example, chloroethane and the like, cannot be compared with this reaction because normal halogenoalkyl compounds and α-halogenoalkyl ethers are different classes of substances with different properties and reactivities.

In principle, all possible primary or secondary amides of aliphatic, araliphatic or aromatic carboxylic acids, or cyclic carboxamides (lactams) which are not capable of forming an aromatic system in the same way as, for example, pyridin-2-one or cytosine or the like, are used as starting compounds for the process. Concrete examples of such starting compounds are:

HCONH$_2$
HCONHCH$_3$
HCONHC$_3$H$_7$(n)
CH$_3$CONHCH$_3$
(CH$_3$O)$_2$CH-CONH$_2$
CH$_3$CONHC$_4$H$_9$(i)
ClCH$_2$CONHC$_2$H$_5$
Cl$_2$CHCONH$_2$
Cl$_3$CCONHCH$_3$
BrCH$_2$CONHCH$_3$
C$_2$H$_5$CONHCH$_3$
C$_3$H$_7$CONHC$_2$H$_5$
C$_7$H$_{15}$CONHCH$_3$
CH$_3$OCH$_2$CONHCH$_3$
C$_6$H$_5$OCH$_2$CONHCH$_3$
CH$_3$OOC—CH$_2$—CONH$_2$
C$_2$H$_5$OOC—(CH$_2$)$_4$—CONH$_2$
CH$_3$OOC—CH=CH—CONH$_2$
C$_6$H$_5$—CH$_2$CONHCH$_3$
p—ClC$_6$H$_4$—CH$_2$CONHCH$_3$
C$_6$H$_5$CONHC$_2$H$_5$
n—CH$_3$C$_6$H$_4$CONHCH$_3$

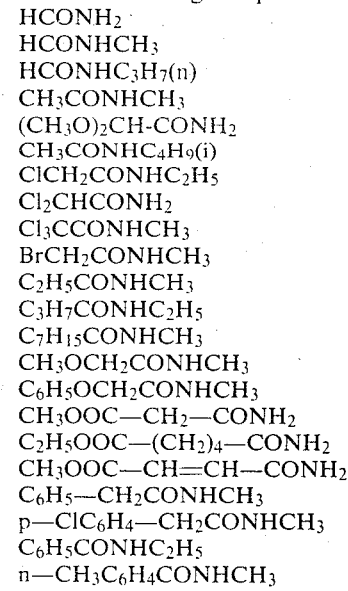
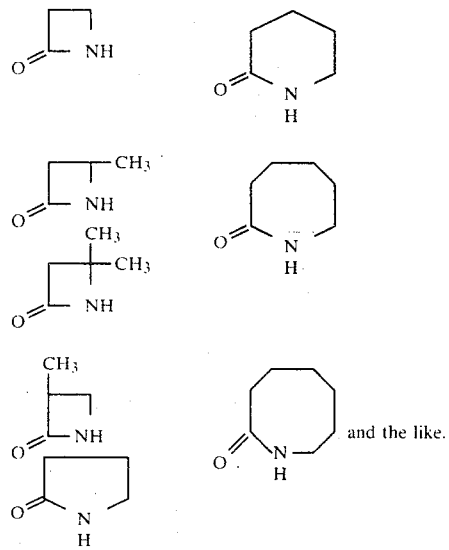

and the like.

Preferred starting compounds are the primary and secondary carboxamides (including lactams) which are represented by the following formula I:

$$R^1-CON\begin{matrix}R^2\\H\end{matrix} \quad (I)$$

wherein $R^1$=H or C$_1$-C$_4$—alkyl optionally substituted by groups which are inert towards the reaction, $R^2$=H or C$_1$-C$_3$—alkyl, or $R^1$+$R^2$ together=an alkylene group with 2 to 6 C atoms in the chain, optionally substituted by groups which are inert towards the reaction.

The expression "groups which are inert towards the reaction" is to be understood as meaning those groups which do not enter into any reaction under the reaction conditions used, that is to say, for example, alkyl groups (preferably $C_1$-$C_4$-alkyl), alkoxy groups (also preferably with 1 to 4 C atoms), the phenoxy group, F, Cl, Br and the like.

Particularly preferred primary and secondary carboxamides are those compounds of the formula I wherein $R^1$=H, $CH_3$ or $C_2H_5$ and $R^2$=H, $CH_3$ or $C_2H_5$.

Examples of suitable open-chain α-halogenoalkyl ethers with at least 3 C atoms per molecule are $CH_3$—CHCl—O—$CH_3$
$CH_3$—CHCl—O—$C_2H_5$
$CH_3$—CHCl—O—$C_3H_7$(n)
$CH_3$—CHCl—O—$C_4H_9$(i)
$C_2H_5$—CHCl—O—$CH_3$
(i-)$C_3H_7$—CHCl—O—$CH_3$
$CH_3$—CHCl—O—$CH_2$—$C_6H_5$
$CH_3$—CHBr—O—$C_2H_5$ and the like.

Preferred open-chain α-halogenoalkyl ethers are the compounds represented by the following formula II:

$$X-\underset{OR^4}{\underset{|}{CH}}-R^3 \qquad (II)$$

wherein $R^3$=($C_1$-$C_4$)—alkyl, $R^4$ also=($C_1$-$C_4$)—alkyl, and X=Cl or Br, preferably Cl.

These α-halogenoalkyl ethers are obtainable in accordance with known methods, for example by the addition of a hydrogen halide onto vinyl ethers, the α-chlorination of dialkyl ethers, the reaction of acetals with acid chlorides or the reaction of aldehydes with alcohols and a hydrogen halide. Amongst these, the last-mentioned method is preferred because of the simple starting materials and procedure and also because of the good yields. The reaction equation on which this method is based is (for the preparation of the preferred α-halogenoalkyl ethers of the formula II):

$$R^3CHO + R^4OH + HX \longrightarrow X-\underset{OR^4}{\underset{|}{CH}}-R^3 + H_2O$$

In the formulae, the radicals $R^3$, $R^4$ and X have the same meaning as in formula II.

In principle, all possible tertiary amines, such as, for example, ($CH_3$)$_3$N
($C_2H_5$)$_3$N
($CH_3$)$_2$N—$CH_2$—$CH_2$—N($CH_3$)$_2$
($CH_3$)$_2$N—($CH_2$)$_2$—N($CH_3$)—($CH_2$)$_2$—N($CH_3$)$_2$,
permethylated polyethyleneimines,
($CH_3$)$_2$N—$CH_2$—$COOC_4H_9$,

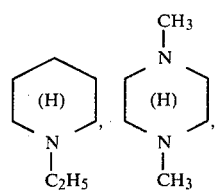

diazabicyclooctane (DABCO),

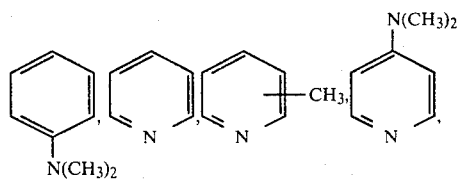

basic ion exchangers with tertiary amino groups, and the like, can be employed as tertiary amines for the process according to the invention.

Preferred tertiary amines are those tertiary monoamines and/or polyamines which contain 3 to 20, preferably 3 to 10, C atoms in the molecule per N atom. Particularly preferred tertiary amines are trimethylamine and triethylamine, in particular triethylamine.

The reactants, namely the primary or secondary carboxamide, the open-chain α-halogenoalkyl ether and the tertiary amine, are to be reacted in a ratio such that about 1 mole of open-chain α-halogenoalkyl ether and about 1 equivalent (=molecular weight/number of N atoms in the molecule) of tertiary amine are present per mole of primary or secondary carboxamide; preferably, the α-halogenoalkyl ether is employed in a slight excess, which can be between about 0.1 and 2 moles per mole of carboxamide, and the tertiary amine is employed in an amount equivalent to the amount of the α-halogenoalkyl ether. However, it is also possible to work with an excess of carboxamide and then to recycle the unconverted carboxamide into the reaction, but this is to no advantage.

If the preferred starting materials of the formulae I and II are employed for the process, the reaction can be represented by the following equation (only $N\!\!-\!\!\!\overset{\diagup}{\diagdown}$ being written for the tertiary amine):

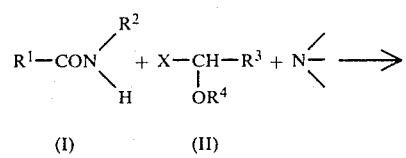

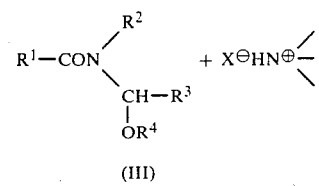

The resulting (secondary and tertiary) N-α-alkoxyalkyl-carboxamides then have the formula III. In all formulae, the radicals $R^1$-$R^4$ and X have the meaning previously indicated for the formulae I and II.

If a primary carboxamide is used as the starting carboxamide and about 2 moles of the α-halogenoether and about 2 equivalents of tertiary amine, instead of 1 mole of open-chain α-halogenoether and 1 equivalent of tertiary amine, are employed per mole of the said primary carboxamide, it is also possible to obtain the carboxamides bis-α-alkoxy-alkylated on the N. With the preferred starting materials of the formula I (in which, however, $R^2$ can only be H in this case) and of the formula II, the reaction then proceeds in accordance with the following equation:

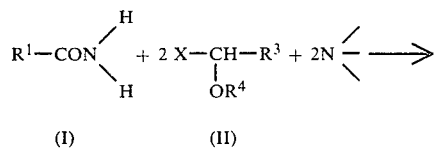

(I)    (II)

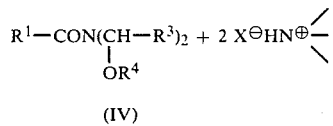

(IV)

The resulting N,N-bis-α-alkoxyalkyl-carboxamides have the formula IV. In all formulae, the radicals $R^1$, $R^3$, $R^4$ and X again have the meaning previously indicated for the formulae I and II.

The reaction according to the invention is advantageously carried out with the addition of a solvent or diluent because, as a rule, the halide of the tertiary amine used precipitates in solid form during the reaction. The reactants themselves, that is to say either the starting carboxamide or the corresponding open-chain α-halogenoalkyl ether or the tertiary amine, can be used as the solvent or diluent. The reaction product, that is to say the particular N-α-alkoxyalkyl-carboxamide, can also be used as the solvent or diluent.

Other suitable solvents or diluents are virtually all inert organic solvents, such as aliphatic and aromatic hydrocarbons (pentane, hexane, octane, light petroleum, ligroin, cyclohexane, benzene, toluene and the like), aliphatic and aromatic halogenohydrocarbons, in particular chlorohydrocarbons (methylene chloride, carbon tetrachloride, chlorobenzene and the like), aliphatic ethers (diethyl ether, diisopropyl ether, tetrahydrofuran and the like), esters (ethyl acetate, methyl propionate and the like), ketones (acetone, methyl ethyl ketone and the like), nitriles (acetonitrile, n-butyronitrile and the like), and so on.

The choice of the special solvent or diluent is essentially determined by the nature of the reaction procedure and the working-up; it is not necessary for all the reactants to be soluble in the chosen solvent or diluent.

In principle, the reactants can be added in any desired order. Care should be taken only to ensure that the starting carboxamide and α-halogenoalkyl ether do not come together in the presence of traces of acid, because undesired side reactions can then occur. It is therefore advantageous to add the tertiary amine to the α-halogenoalkyl ether in an amount which is at least sufficient to bind hydrogen halide which may still be present in the ether (from the preparation of the latter), before the ether is combined with the carboxamide.

Thus, for example, the starting carboxamide and the tertiary amine can be introduced initially and the α-halogenoalkyl ether metered in, or the α-halogenoalkyl ether and the tertiary amine can be introduced initially and the carboxamide metered in, or also the α-halogenoalkyl ether can be introduced initially and the carboxamide and the tertiary amine added in any desired order.

It is furthermore possible for all the reactants to be metered into the reaction vessel simultaneously.

Particularly advantageously, the reaction can be carried out by simultaneously adding the amounts of carboxamide and tertiary amine required for the reaction according to the invention, separately or in a mixture, to the open-chain α-halogenoalkyl ether prepared in a known manner, preferably from aldehyde, alcohol and hydrogen halide, after neutralization by means of tertiary amine in the same reaction vessel in which the ether was prepared, because this procedure makes it possible to carry out the reaction virtually as a "one-spot process".

The reaction temperature essentially depends on the reactivity of the reactants. In general, the reaction can be carried out in a temperature range between about $-20°$ and about $+60°$ C. Above this range, the yield usually drops gradually, whilst below the range, the reaction usually becomes too slow and takes too long.

To work up the reaction batch, the resulting hydrohalide of the tertiary amine employed can be directly filtered off and the filtrate concentrated and distilled. However, it is also possible to add bases, preferably alkali metal and alkaline earth metal hydroxides and carbonates (for example NaOH, KOH, $Na_2CO_3$, Ca-$(OH)_2$ and the like) to the batch and thus to liberate the tertiary amine in the reaction mixture again. The amine can then be recovered, for example by distillation.

The process according to the invention makes it possible to prepare N-α-alkoxyalkyl-carboxamides (including lactams and N,N-bis-α-alkoxyalkyl-carboxamides) from simple, readily accessible and hence inexpensive starting materials, without significant technical effort and virtually without environmental pollution, in high yields, and therefore represents a considerable advance.

Furthermore, the products of the process, of the following formulae V and VI, are new compounds:

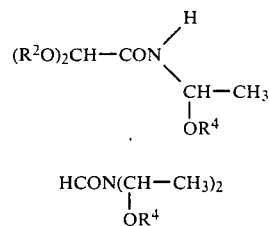

In both formulae, $R^4$ has the meaning indicated for formula II, that is to say $(C_1-C_4)$-alkyl, the meaning $R^4=CH_3$ being preferred in this case; $R^5$ (in formula V) denotes $CH_3$ or $C_2H_5$.

Examples of compounds of the formula V are:

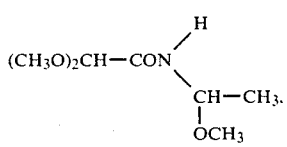

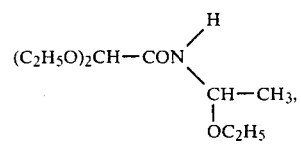

-continued

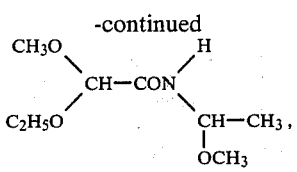

and the like,
and examples of compounds of the formula VI are:

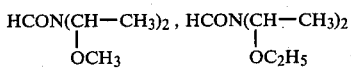

and the like.

The compounds obtained by the process according to the invention are intermediates mainly for the preparation of N-alkenyl-(in particular N-vinyl-)carboxamides, such as, for example, N-vinyl-methyl-acetamide, which, as already mentioned in the introduction, can in turn be processed primarily to give valuable homopolymers and copolymers. The conversion of the N-α-alkoxyalkyl-carboxamides to the corresponding N-alkenyl- or N-vinyl-carboxamides is carried out in a known manner, preferably by heating to temperatures of about 60° to 350° C., usually in the presence of catalysts (German Patent Specification 1,235,893, U.S. Pat. No. 3,377,340, British Patent Specification No. 1,125,324, German Offenlegungsschrift No. 2,336,977 and the like). The same applies to the N,N-bis-α-alkoxyalkyl-carboxamides. The N-vinyl compounds resulting from the splitting-off of alkanol from the N-α-alkoxyethyl compounds of the formula V are also new; they have the formula VII:

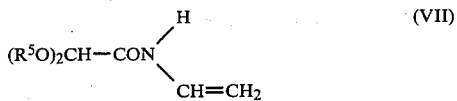

wherein $R^5$ has the same meaning as in Formula V.
Formula VII therefore represents:

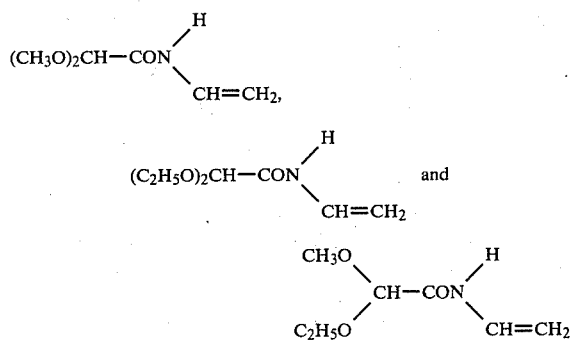

The invention is now illustrated in greater detail by the following examples. The examples according to the invention (A) are followed by 2 examples (B) of the splitting-off of alcohol from products obtained by the process according to the invention, to give the corresponding N-vinyl products, an example (C) of the (co-)polymerization of said N-vinylproducts and also by a comparison example (D) which shows that the reaction of pyridin-2-one with α-chloro-tetrahydrofuran, known from Tetrahedron Letters, 1976, 1,725 to 1,728, no longer "goes" if the pyridin-2-one is replaced by a "normal" carboxamide.

(A) Examples according to the invention

EXAMPLE 1

N-α-Methoxyethyl-N-ethyl-formamide 8.0 g of triethylamine and then a mixture of 42.5 g of triethylamine (0.5 mole in total) and 14.6 g (0.2 mole) of N-ethylformamide are added dropwise, at 0° C., to a mixture of 60 ml of light petroleum and 38 g (0.4 mole) of α-chloroethyl methyl ether.

After 2 hours, the mixture is filtered while ice-cold, the filter cake is washed with hexane and the filtrate is concentrated in vacuo. The residue is subjected to flash distillation. This yields 19.8 g (76% of theory) of N-α-methoxyethyl-N-ethylformamide with a boiling point (20 mm Hg) of 89°–91° C. $^1$H-NMR (CDCl$_3$): 1.15 ppm (t); 1.4 ppm (d); 3.15 ppm (s); 3.25 ppm (q); 4.6 ppm (q); 5.55 ppm (q); 8.12 ppm (s); 8.22 ppm (s).

EXAMPLE 2

N-α-Methoxyethylacetamide

First 7.3 g of triethylamine and then simultaneously, from two dropping funnels, 11.8 g (0.2 mole) of acetamide, dissolved in 30 ml of acetonitrile, and 44 g of triethylamine (total amount: 0.5 mole) are added dropwise, at −10° C., to a mixture of 30 ml of acetonitrile and 38 g (0.4 mole) of α-chloroethyl methyl ether. Two hours after the dropwise introduction has ended, the mixture is filtered, the solvent is removed in vacuo, the residue is extracted with i-propyl ether and the extract is again concentrated on a rotary evaporator. The residue is subjected to flash distillation. Boiling point (0.2 mm Hg): 60°–62° C. Yield: 17.6 g=75% of N-α-methoxyethyl-acetamide. $^1$H-NMR (CDCl$_3$): 1.3 ppm (d); 2.0 ppm (s); 3.3 ppm (s); 5.0–5.5 ppm (m); 6.25 ppm (broad).

EXAMPLE 3

N-α-(i-Butoxy)-ethyl-N-methyl-acetamide

A mixture of 91 g of triethylamine and 36.5 g (0.5 mol) of N-methylacetamide is added dropwise, at 0° C., to a mixture of 136.5 g (1 mole) of i-butyl α-chloroethyl ether, 130 ml of hexane and 20 g of triethylamine (1.1 moles in total).

2 hours after the dropwise introduction has ended, 40 g of technical-grade sodium hydroxide flakes and 20 ml of 50% strength sodium hydroxide solution are added in small portions at 0° C., the mixture is stirred for a further 30 minutes, the hexane solution is decanted and the flask is rinsed with hexane. The solvent and the liberated triethylamine are stripped off in vacuo from the filtered hexane solution and the residue is distilled in vacuo. Boiling point (2 mm Hg): 56° C. Yield: 58 g (67% of theory). $^1$H-NMR (CDCl$_3$): 1.0 ppm (d); 2.25 ppm (dd); 1.6–2.0 ppm (m); 2.15 ppm (d); 2.85 ppm (d); 3.15 ppm (d); 5.1 ppm (q); 5.9 ppm (q).

EXAMPLE 4

N-α-Methoxyethyl-N-methyl-acetamide

First 20 g of triethylamine and then a mixture of 91 g of triethylamine (1.1 moles in total) and 36.5 g (0.5 mole) of N-methylacetamide are added dropwise, at 0° C., to a solution of 94.5 g (1 mole) of α-chloroethyl methyl ether in 200 ml of hexane. After 2 hours, 44 g (1.1 moles) of technical-grade sodium hydroxide flakes are added and 20 ml of 50% strength sodium hydroxide solution are added dropwise, whilst cooling with ice, and the mixture is stirred for a further half an hour. The hexane solution is decanted, the flask is rinsed with hexane and the reaction solution is concentrated, the triethylamine employed being completely recovered in the distillate. The residue is subjected to flash distillation in vacuo. This yields 61 g (93% of theory) of N-α-methoxyethyl-N-methyl-acetamide. Boiling point (23 mm Hg): 84° C. $^1$H-NMR (CDCl$_3$): 1.2–1.4 ppm (dd); 2.1 ppm (d); 2.8 ppm (d); 3.2 ppm (d); 4.95–5.15 ppm (q); 5.6–5.9 ppm (q).

EXAMPLE 5

N-α-Ethoxyethyl-N-methylacetamide

A mixture of 50 g (0.5 mole) of triethylamine and 14.6 g (0.2 mole) of N-methylacetamide is added dropwise, at 60° C. in the course of 15 minutes, to a mixture of 44 g (0.4 mole) of α-chloro-diethyl ether and 100 ml of hexane.

After a further 15 minutes, the mixture is cooled in ice and filtered, the filter cake is washed with hexane and, after stripping off the solvent, the reaction product is distilled in vacuo. This yields 23.2 g (80% of theory) of N-α-ethoxyethyl-N-methylacetamide with a boiling point (23 mm Hg) of 94°–95° C. $^1$H-NMR (CDCl$_3$): 1.0–1.4 ppm (m); 2.1 ppm (d); 2.8 ppm (d); 3.3–3.6 ppm (q); 4.9–5.2 ppm (q); 5.7–6.0 ppm (q).

EXAMPLE 6

N-α-Methoxyethyl-N-methylacetamide from acetaldehyde, methanol and N-methylacetamide 59 g (1.6 moles) of dry hydrogen chloride are passed, at 0° C., into a mixture of 49 g (1.1 equivalents) of paraldehyde and 35 g (1.1 moles) of methanol.

160 ml of light petroleum are added and the lower, aqueous layer is removed from the reaction vessel. Excess hydrogen chloride is removed from the upper layer by passing in nitrogen. First 20 g of triethylamine and then a mixture of 91 g of triethylamine (1.1 moles in total) and 36.5 g (0.5 mole) of methylacetamide are added dropwise, at 0° C., to the said upper layer. After 2 hours, 44 g (1.1 moles) of sodium hydroxide flakes are added and 20 ml of 50% strength sodium hydroxide solution are then added dropwise, whilst cooling with ice, and the mixture is stirred for a further 30 minutes. The hexane solution is decanted, the reaction vessel is rinsed with hexane and the reaction solution is concentrated, triethylamine being recovered without loss. The residue is subjected to flash distillation. Yield: 59 g = 90% of theory. For conversion to N-vinyl-N-methylacetamide, the undistilled crude product can be distilled directly into the cracking furnace of Example B.

EXAMPLE 7

N-α-Methoxy-i-butyl-N-methylacetamide

First 15 g of triethylamine and then a mixture of 35.5 g of triethylamine and 14.6 g (0.2 mole) of N-methylacetamide are added dropwise, whilst cooling with ice, to a mixture of 49 g (0.4 mole) of α-chloro-i-butyl methyl ether and 50 ml of light petroleum.

After the reaction has ended, 20 g of solid sodium hydroxide and 10 ml of 50% strength sodium hydroxide solution are added, the mixture is stirred for a further 30 minutes and filtered and, after the triethylamine and solvent have been driven off, the reaction product is distilled. This yields 23.3 g (73% of theory) of N-α-methoxy-i-butyl-N-methylacetamide with a boiling point (0.05 mm Hg) of 53° C.

EXAMPLE 8

1-α-Methoxyethyl-4,4-dimethyl-azetidin-2-one 7.3 g of triethylamine and then a mixture of 19.8 g (0.2 mole) of 4,4-dimethyl-azetidin-2-one and 43.2 g of triethylamine are added dropwise, at 0° C., to a solution of 38 g (0.4 mole) of α-chloroethyl methyl ether in 60 ml of hexane. The mixture is stirred for a further 2 hours at 0° C. and 10 ml of 50% strength sodium hydroxide solution and 20 g of powdered sodium hydroxide are added. After a further 30 minutes, the hexane solution is decanted, the deposit is rinsed with hexane and the hexane extracts are concentrated on a rotary evaporator. This yields 25.5 g (81% of theory) of 1-α-methoxyethyl-4,4-dimethyl-azetidin-2-one. $^1$H-NMR (CDCl$_3$): 1.4 ppm (d); 1.5 ppm (s); 2.75 ppm (s); 3.3 ppm (s); 4.8–5.1 ppm (q).

EXAMPLE 9

N-α-Methoxyethyl-pyrrolidone

First 7.3 g of triethylamine and then simultaneously, from two dropping funnels, 43.2 g of triethylamine and a solution of 17 g (0.2 mole) of pyrrolidone in 40 ml of methylene chloride are added dropwise, at 0° C., to a solution of 38 g (0.4 mole) of α-chloroethyl methyl ether in 30 ml of methylene chloride.

2 hours after the dropwise introduction has ended, the mixture is stirred for 1 hour with a slurry of 30 g of powdered potassium hydroxide in 15 ml of 50% strength potassium hydroxide solution. The methylene chloride solution is decanted, the residue is extracted with methylene chloride and the methylene chloride solution is concentrated in vacuo. This yields 22.3 g (78% of theory) of N-α-methoxyethyl-pyrrolidone. $^1$H-NMR (CDCl$_3$): 1.3 ppm (d); 1.8–2.6 ppm (m); 3.2 ppm (s); 3.1–3.5 ppm (m); 5.1–5.5 ppm (q).

EXAMPLE 10

α,α-Dimethoxyacetic acid N-α'-methoxy-ethylamide 200 g of gaseous hydrogen chloride are passed, at 10° C., into a mixture of 176 g (4 equivalents) of paraldehyde and 144 g (4.5 moles) of methanol. After separating off the lower liquid layer, excess hydrogen chloride is removed from the upper layer by passing in dry nitrogen. 200 ml of acetonitrile and 47 g of triethylamine are added. 454.2 g (4.4 moles) of triethylamine and a solution of 238 g (2 moles) of dimethoxyacetamide in 380 ml of acetonitrile are then simultaneously added dropwise at 0° to 10° C. After the dropwise addition has ended, the reaction is stirred for a further 3 hours at room temperature and 2 hours at 50° C. At 20° C., 720 g (6 moles) of 33% strength sodium hydroxide solution are then added to the batch and the mixture is stirred for 30 minutes. The lower layer is then separated off and extracted twice with acetonitrile. The combined acetonitrile solutions are concentrated on a rotary evaporator and the residue is distilled in vacuo. This yields 325 g (92% of theory) of α,α-dimethoxyacetic acid N-α'-methoxy-ethylamide with a boiling point (0.7 mm Hg) of 78°–82° C. $^1$N-NMR (CDCl$_3$): 1.35 (d,J=6 Hz); 3.3 (s); 3.4 (s); 4.7 (s); 5.1–5.5 (m); 6.8 (broad) ppm. Intensity ratio: 3:3:6:1:1:1.

$C_7H_{15}NO_4$ (177.20): Calculated C: 47.44; H: 8.5; N: 7.90. Found C: 47.7; H: 8.5; N: 7.7.

The α,α-dimethoxyacetamide employed as the starting material was obtained from methyl α,α-dimethoxyacetate by reaction with aqueous ammonia. Melting point: 69°–70° (ethyl acetate).

EXAMPLE 11

N,N-Di-(α-methoxyethyl)-formamide and N-α-methoxyethylformamide

α-Chloroethyl methyl ether is prepared, as in Example 10, from 2 equivalents of paraldehyde, 2.2 moles of methanol and 2.7 moles of hydrogen chloride. The said ether is diluted with 100 ml of acetonitrile. 250.3 g (2.5 moles) of triethylamine and a solution of 45 g (1 mole) of formamide in 265 ml of acetonitrile are then simultaneously added dropwise at 0° C.

After the dropwise addition has ended, the mixture is stirred for a further 3 hours at room temperature and 2 hours at 50° C., stirred with 360 g (3 moles) of 33% strength sodium hydroxide solution for 30 minutes and separated, the aqueous layer is extracted twice with acetonitrile and the acetonitrile solution is concentrated on a rotary evaporator.

The crude reaction product is extracted with hexane. After distilling off the solvent, the hexane-soluble portion is distilled in vacuo. This yields 83 g (50% of theory) of N,N-di-(α-methoxyethyl)-formamide with a melting point (0.1 mm Hg) of 50°–52°. $^1$H-NMR (CDCl$_3$): 1.2–1.6 (m); 3.2–3.4 (m); 4.5–4.8 (m); 5.5–5.8 (m); 8.45 (s)–8.55 (s). Intensity ratio: 6:6:1:1:1.

By fractionation of the hexane-insoluble residue from the crude reaction product, 24 g (23% of theory) of N-α-methoxy-ethyl-formamide with a boiling point (0.5 mm Hg) of 60°–62° are obtained.

According to the $^1$H-NMR spectrum and thin layer chromatography (silica gel, eluant: 90% of chloroform, 10% of methanol), the product is identical to N-α-methoxyethylformamide which has been prepared electrochemically according to Patent Application Ser. No. 149,742 filed May 14, 1980, Examples 1–7, Table 1.

If the reaction is carried out by initially introducing a mixture of 90 g (2 moles) of formamide, 253 g (2.5 moles) of diethylamine and 341 ml of acetonitrile and adding 189 g (2 moles) of α-chloroethyl methyl ether dropwise at room temperature, N-α-methoxyethyl-formamide is then obtained as the main product, the working-up conditions for the batch being the same.

(B) Splitting-off of alcohol

Example 1: N-Vinyl-N-methyl-acetamide

In a thin film evaporator, N-α-methoxyethyl-N-methylacetamide is evaporated at 270° C. under a nitrogen blanket. The vapor is passed through a furnace filled with a porous silica as a catalyst. The cracked products are condensed at the end of the furnace. Table 1 shows the content of uncracked starting material in the condensate as a function of the furnace temperature, the throughput being 400 g of starting material/hour.

| Temperature (°C.) | N-α-Methoxyethyl-N-methyl-acetamide, residual content (%) |
| --- | --- |
| 225 | 3.3 |
| 240 | 2.0 |
| 250 | 1.7 |
| 265 | 0.4 |
| 280 | 0.3 |
| 290 | 0.3 |

The total yields of N-vinyl-N-methylacetamide and uncracked starting material are 97–98%.

The crude cracked material is rectified in a packed column. After distilling off the methanol which has been split off, N-vinyl-N-methylacetamide with a boiling point (11 mm Hg) of 51.5° C. is obtained in quantitative yield.

Example 2: α,α-Dimethoxyacetic acid N-vinylamide

By following the same procedure as in the previous example, α,α-dimethoxyacetic acid N-α-methoxyethylamide (preparation, see Example 10) is converted to α,α-dimethoxyacetic acid N-vinylamide at 300° C. The yield is 95% of theory with a conversion of over 99%.

The vinyl compound is obtained in the same yield by carrying out the reaction at 100 mm Hg, the furnace temperature likewise being 300° C. The evaporator is only heated to 220° C. in this case.

α,α-Dimethoxyacetic acid N-vinylamide boils at 64° C./0.1 mm Hg. NMR spectrum (CDCl$_3$): 3.4 (s); 4.4–4.8 (2 d); 4.7 (s); 6.6–7.3 (m); 8.2 (broad) (ppm). Intensity ratio: 6:2:1:1:1.

(C) (Co−) polymerization of the N-Vinyl-compounds

In a 1 l glass vessel, provided with stirrer, thermometer and gas-inlet tube, 18 parts (by weight) of acrylamide CH$_2$=CH—CONH$_2$ are dissolved in 450 parts of water. The clear solution is adjusted to pH 8–9 with NaOH. To this solution 2 parts of α,α-dimethoxyacetic acid N-vinylamide (preparation see B-Example 2) are added. Thereafter N$_2$ is passed through the solution during 30 minutes at room temperature while stirring; the solution is, then, heated to 50° C. and at this temperature 0.11 part of azoisobutyronitrile (dissolved in 0.6 part of dimethyl formamide) is added. After about 60 minutes polymerization begins, which is to be seen by a slight increase of the temperature as well as of the viscosity. The polymerization is finished after 3 hours. The transparent polymerization product has Brookfield-viscosity of 4300 cps (=centipoise) at a rotation speed of 6 (rotations)/minute, of 3950 cps at 12 rotations/minute, and of 3300 cps at 30 rotations/minute.

Owing to the decrease of viscosity with increasing rotation speed (=thixotropy), the polymer can be used where thixotropic substances are needed.

Furthermore, the polymer is a valuable padding auxiliary with a migration-preventing effect in the dyeing field, therefy promoting excellently uniform dyeing of the respective substrates, especially of textile articles when dyed by the thermosol process.

(D) Comparison Example 5.4 g (40 mmoles) of sulfuryl chloride are dissolved in 40 ml of anhydrous tetrahydrofuran. After the reaction has ended, half of this solution is first added to a mixture of 1.46 g (20 mmoles) of N-methylacetamide and 9.09 g (90 mmoles) of anhydrous triethylamine in 40 ml of anhydrous tetrahydrofuran.

After 15 minutes, the remainder of the reacted sulfuryl chloride solution is added. After a further 15 minutes, the mixture is cooled in ice and filtered, the filtrate is concentrated on a rotary evaporator, the residue is extracted with light petroleum, the extract is dried over $MgSO_4$ and again concentrated to dryness on a rotary evaporator, and the residue (1.12 g) is distilled in vacuo. In addition to resinified undistilled residue, this yields 0.22 g of impure distillate which, according to $^1$H-NMR (broad signal at 7.3 ppm) and the IR spectrum (amide II bands at 1,540 $cm^{-1}$, NH bands at 3,330 $cm^{-1}$), consists essentially of amides which still carry a hydrogen atom on the nitrogen atom.

I claim:

1. A process for the preparation of N-α-alkoxyalkyl-carboxamides starting from primary or secondary carboxamides, which comprises reacting primary or secondary amides of aliphatic, araliphatic or aromatic carboxylic acids, or cyclic carboxamides (lactams) which are not capable of forming an aromatic system, with open-chain α-halogenoalkyl ethers with at least 3 C atoms per molecule, in the presence of tertiary amines.

2. A process as claimed in claim 1, wherein compounds of the formula I

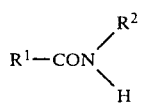   (I)

wherein $R^1$=H or $C_1$-$C_4$-alkyl optionally substituted by groups which are inert towards the reaction, $R^2$=H or $C_1$-$C_3$-alkyl, or $R^1$+$R^2$ together=an alkylene group with 2–6 C atoms in the chain, optionally substituted by groups which are inert towards the reaction, are used as the primary or secondary carboxamides.

3. A process as claimed in claims 1 and 2, wherein compounds of the formula I in which $R^1$=H, $CH_3$ or $C_2H_5$ and $R^2$=H, $CH_3$ or $C_2H_5$ are used as the primary or secondary carboxamides.

4. A process as claimed in claims 1 to 3, wherein compounds of the formula II $$X-CH-R^3 \atop OR^4 \qquad (II)$$

wherein $R^3$=($C_1$-$C_4$)-alkyl, $R^4$ also=($C_1$-$C_4$)-alkyl, and X=Cl or Br, preferably Cl, are used as the open-chain α-halogenoalkyl ethers with at least 3 C atoms per molecule.

5. A process as claimed in claims 1 to 4, wherein those tertiary monoamines or polyamines which contain 3 to 20, preferably 3 to 10, C atoms in the molecular per N atom are used as the tertiary amines.

6. A process as claimed in claims 1 to 5, wherein trimethylamine and/or triethylamine, preferably triethylamine, are used as the tertiary amines.

7. A process as claimed in claims 1 to 6, wherein the open-chain α-halogenoalkyl ethers are prepared in situ, in a known manner, from aldehyde, alcohol and hydrogen halide and, after neutralization of the reaction solution by means of tertiary amine, the primary or secondary carboxamide and additional tertiary amine are metered in.

8. A process as claimed in claims 1 to 7, wherein the reaction is carried out in the temperature range between about −20° and +60° C.

9. Compounds of the formula V:

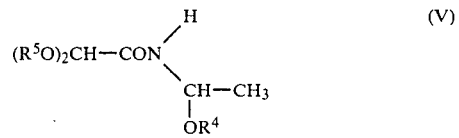   (V)

wherein $R^4$=($C_1$-$C_4$)-alkyl, preferably $CH_3$, and $R^5$=$CH_3$ or $C_2H_5$.

10. Compounds of the formula VI:

   (VI)

wherein $R^4$ has the same meaning as in formula V.

11. Compounds of the formula VII:

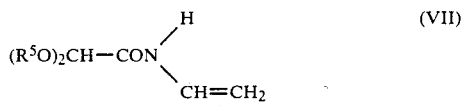   (VII)

wherein $R^5$ has the same meaning as in formula V (=$CH_3$ or $C_2H_5$).

* * * * *